(12) United States Patent
Wang et al.

(10) Patent No.: US 9,750,835 B2
(45) Date of Patent: Sep. 5, 2017

(54) LIQUID DISPENSER WITH SANITIZING CONTROL FUNCTIONS

(71) Applicant: MTN Products, Inc., LaVerne, CA (US)

(72) Inventors: Chun-Yen Wang, El Paso, TX (US); Gregory N Spear, Los Angeles, CA (US)

(73) Assignee: MTN Products, Inc., LaVerne, CA (US)

( * ) Notice: Subject to any disclaimer, the term of this patent is extended or adjusted under 35 U.S.C. 154(b) by 0 days.

(21) Appl. No.: 15/278,382

(22) Filed: Sep. 28, 2016

(65) Prior Publication Data
US 2017/0049918 A1    Feb. 23, 2017

Related U.S. Application Data

(63) Continuation of application No. 13/447,764, filed on Apr. 16, 2012, now Pat. No. 9,480,762, which is a continuation-in-part of application No. 13/445,030, filed on Apr. 12, 2012, now abandoned.

(51) Int. Cl.
| | | |
|---|---|---|
| *A61L 2/18* | (2006.01) | |
| *A61L 2/24* | (2006.01) | |
| *A61L 2/06* | (2006.01) | |
| *A61L 2/07* | (2006.01) | |
| *C02F 1/78* | (2006.01) | |
| *A61L 2/20* | (2006.01) | |
| *B67D 1/00* | (2006.01) | |
| *B67D 3/00* | (2006.01) | |

(52) U.S. Cl.
CPC ........ *A61L 2/24* (2013.01); *A61L 2/06* (2013.01); *A61L 2/07* (2013.01); *A61L 2/18* (2013.01); *A61L 2/183* (2013.01); *A61L 2/202* (2013.01); *B67D 1/0004* (2013.01); *B67D 3/00* (2013.01); *C02F 1/78* (2013.01); *A61L 2202/12* (2013.01); *A61L 2202/14* (2013.01); *B67D 2001/0094* (2013.01); *B67D 2210/00013* (2013.01); *C02F 2303/04* (2013.01)

(58) Field of Classification Search
CPC ... A61L 2/18; A61L 2/20; A61L 2/183; A61L 2/202
See application file for complete search history.

(56) References Cited

U.S. PATENT DOCUMENTS

| | | | |
|---|---|---|---|
| 6,207,046 B1 * | 3/2001 | Yamashita | B67D 1/07 210/138 |
| 6,561,382 B2 * | 5/2003 | Shelton | A61L 2/202 210/760 |
| 2003/0071069 A1 * | 4/2003 | Shelton | C02F 1/78 222/190 |

* cited by examiner

*Primary Examiner* — Sean E Conley
(74) *Attorney, Agent, or Firm* — Michael P Mazza, LLC

(57) ABSTRACT

Liquid dispensing systems which automatically sanitize the liquid and liquid-contacting parts of a liquid dispensing system, by periodically flushing the system with a sufficiently heated, liquid and/or gas.

11 Claims, 5 Drawing Sheets

LIQUID DISPENSER WITH SANITIZING CONTROL FUNCTIONS

REQUEST FOR PRIORITY

This is a continuation of U.S. Ser. No. 13/447,764, now U.S. Pat. No. 9,480,762, titled "Liquid Dispenser With Sanitizing Control Functions," filed on Apr. 12, 2012, which is a continuation-in-part of U.S. Ser. No. 13/445,030.

INCORPORATION BY REFERENCE

The following copending patents and patent applications are incorporated by reference in their entirety into this patent application: co-pending U.S. Pat. No. 7,434,603 ("BL 1"); U.S. Pat. No. 8,281,821, issued Oct. 9, 2012 and titled "Bottom Load Water Cooler" ("BL 3"); and U.S. Pat. No. 8,356,731, issued Jan. 22, 2013 and titled "Energy Saving Baffle For Water Cooler".

BACKGROUND OF THE INVENTION

The present invention generally relates to water coolers drawing water from either a bottle, or from point-of-use (POU) filtered water. More specifically, the invention relates to systems and apparatus with hot water or hot gas sanitizing functions.

Two main dispensing methods are used to dispense water or another liquid from a water cooler to a vessel such as a cup or glass: gravity-fed and pump-fed methods. With gravity-fed methods, a dispensing nozzle is positioned sufficiently lower than the water level of the water tank to allow water to be dispensed to the vessel at a desired flow rate based on gravity. With pump-fed systems, the dispensing nozzle may be positioned higher than the water level of the tank, and a pump or similar apparatus may be used to cause the liquid to flow to the nozzle area at a desired flow rate for dispensing to the vessel. In addition to a pump, electronics and valves are usually needed with pump-fed systems.

Gravity-fed systems typically position a faucet or other dispensing nozzle close to the water tank, so there is usually less variation in temperature between the liquid in the tank and the liquid being dispensed from the faucet, than in pump-fed systems. However, in both types of systems, this can be an issue. In addition, experience in the water cooler and liquid dispensing industry has shown that water cooler assemblies and liquid dispensing apparatus with sanitizing functions would be advantageous for enhanced pathogen control.

DEFINITION OF CLAIM TERMS

The following terms are used in the claims of the patent as filed and are intended to have their broadest meaning consistent with the requirements of law. Where alternative meanings are possible, the broadest meaning is intended. All words used in the claims are intended to be used in the normal, customary usage of grammar and the English language.

"Sanitize" means to heat a liquid or gas to a sufficient temperature, or to apply a pathogen-killing material such as ozone, sufficient to kill pathogens in a liquid to be dispensed, to ensure the safety of liquid for ingestion by humans. As to heated water or steam, "sanitize" means heating the water to at least between 165° F.-180° F., for a sufficient time period to accomplish this result, and consistent with United States FDA specifications (Food Establishment Plan Review Guide—Section III, Part 9).

"Waterways" means any pathways (such as but not limited to tubing or "liquid communication means") through which liquid in a liquid dispensing system runs, including cold and hot waterways, pumps, solenoid valves and other wetted parts. ("Liquid" as used here is not limited to "water," and may include fruit juices and other non-alcoholic as well as alcoholic beverages.) As an example, in the preferred embodiment described below, all the waterways may be sanitized by either heated or ozonated water in the "Full Clean" mode described below, as the heated or ozonated water will be circulated through the normal dispensing cold water pathways, and also through the faucet/nozzle/dispensing mechanism. As a further example, in the "Auto Clean Mode" described below, there may be a small section (from the valve to the nozzle, for example) which may not be sanitized. (The hot water path, including the dispensing mechanism, will be sanitized every time hot water is dispensed, so there is no need to separately sanitize the hot waterways in this mode.)

SUMMARY OF THE INVENTION

The objects mentioned above, as well as other objects, are solved by the present invention, which overcomes disadvantages of prior water cooler assemblies and liquid dispensing apparatus, while providing new advantages not believed associated with such assemblies and apparatus.

In one group of preferred embodiments, discussed below, a liquid dispensing system is disclosed in which a hot liquid or hot gas, such as hot water or steam, may be periodically, automatically introduced to the liquid dispensing system to auto-sanitize the waterways and reservoirs of the system, including wetted, liquid-contacting parts of the system. ("Automatically" sanitizing in this context means without the need for human intervention, and is to be distinguished from any manual process in which the dispensing system is taken off-line, and brought to an external steam generator, for example, to be cleaned.)

In a particularly preferred embodiment of the invention, a pump-fed, liquid dispensing system may be provided with at least one liquid storage tank (e.g., a cold tank containing a chilled liquid such as water). A first liquid communication means, such as plastic or stainless steel tubing, may be provided to allow the liquid to flow along a first path between the liquid storage tank and a dispenser. A first valve may be located along this first path. A second liquid communication means may be provided to allow the liquid to flow from the first valve to the storage tank. One or more pumps may be used to selectively draw the liquid from the storage tank and cause it to flow along the first path, as controlled by the user.

The foregoing system may also be provided with multiple reservoirs or tanks (e.g., cold and hot tanks), and a second liquid communication means may be provided to allow the liquid to flow along a second path between the second (e.g.) hot tank and either the same or a different dispenser. A second valve may be located along the second path. A third liquid communication means may be provided to allow the liquid to flow from the second valve to the first (e.g., cold) tank. The one or more pumps (such as but not limited to a dedicated cold water pump and a dedicated hot water pump) may be used to selectively draw the liquid from the hot tank and to cause it to flow along the second path, as controlled by the user. This sanitization process is preferably accomplished automatically, either at predetermined periodic intervals, or as the user may select the sanitizing mode to occur.

Alternatively, in another embodiment of the present invention, a gravity-fed liquid dispensing system may be provided. The system may include at least one cold tank containing a chilled liquid, a first liquid communication means allowing the liquid to flow under the influence of gravity, as actuated by a user, along a first path between the at least one cold tank and a dispenser, a first valve located along the first path, and a second liquid communication means allowing the liquid to flow from the first valve to the cold tank. The gravity-fed system may source water from an inverted water bottle in fluid communication with the cold tank, for example. The gravity-fed, liquid dispensing system may also include a hot tank containing heated liquid, a third liquid communication means allowing the liquid to flow along a second path, as actuated by a user, between the hot tank and either the same or a different dispenser, a second valve located along the second path, and a fourth liquid communication means allowing the liquid to flow from the second valve to the cold tank. Again, this sanitization process is preferably accomplished automatically, either at predetermined periodic intervals, or as the user may select the sanitizing mode to occur.

The principles of this embodiment of the present invention may also be employed when water is dispensed from a pressurized system such as a municipal water supply.

Using any of the above-described pressure-fed or gravity systems, a method may be provided for sanitizing all or a portion of the liquid dispensing system. The sanitizing method may include the steps of providing an external or internal (e.g., from the hot tank) source of heated gas or liquid, and using the liquid communication means (e.g., tubing) to allow the heated gas or liquid to flow along various the various liquid paths between cold/hot dispensers/faucets, for example, and between the storage tanks. One or more pumps may be used to selectively draw the liquid from one or the other of the storage tanks and cause it to flow to the dispensers in a selected fashion. When desired, the waterways, including the nozzles/faucets/dispensers, cold tank and other liquid contacting portions, may be hot-water-sanitized by introducing a sufficiently heated liquid or gas (such as heated to at least 80° C. or 176° F.) to contact them.

For example, sanitizing hot water may source from a hot tank used also for drinking, from a dedicated hot tank used only for sanitizing, or from an external source (such as an externally-supplied heated gas such as live steam or heated liquid). If an external sanitizing source is used, a corresponding liquid communication means may be provided. The sanitizing step may also include the step of locking the system against dispensing, and during the lock-out period diverting liquid from the hot tank into the cold tank to eventually raise the temperature of the cold tank to a temperature which will enable the liquid in the cold tank and liquid-contacting parts to be sanitized.

In one preferred embodiment, sanitization may occur periodically in a predetermined fashion in user-defined intervals as controlled by the user. The internal circulation system of the dispensing unit may be used to circulate (e.g.) hot water for at least (e.g.) 30 minutes within the system, for example, to ensure that the sanitizing liquid or gas reaches all wetted parts in the liquid dispensing system, including sufficient contact time. After sanitization is complete, all liquid in the system may be discarded through a connected drain line, or the hot liquid may be transferred to the cold tank for cooling.

BRIEF DESCRIPTION OF THE DRAWINGS

The novel features which are characteristic of the invention are set forth in the appended claims. The invention itself, however, together with further objects and attendant advantages thereof, can be better understood by reference to the following description taken in connection with the accompanying drawings, in which:

The components in the drawings are not necessarily to scale, emphasis instead being placed upon clearly illustrating the principles of the present invention. In the drawings, like reference numerals designate corresponding parts throughout the several views.

DETAILED DESCRIPTION OF THE PREFERRED EMBODIMENTS

Set forth below is a description of what are believed to be the preferred embodiments and/or best examples of the invention claimed. Future and present alternatives and modifications to this preferred embodiment are contemplated. Any alternatives or modifications which make insubstantial changes in function, in purpose, in structure, or in result are intended to be covered by the claims of this patent.

The water cooler systems or liquid dispensing systems of the present invention may utilize any commercially available water coolers or liquid dispensing systems, including those disclosed in the above-referenced patent applications which are incorporated by reference into this application. The specific embodiments discussed below are not intended to narrow the scope of the claimed invention as discussed in the Summary of the Invention, above.

Figure 1:
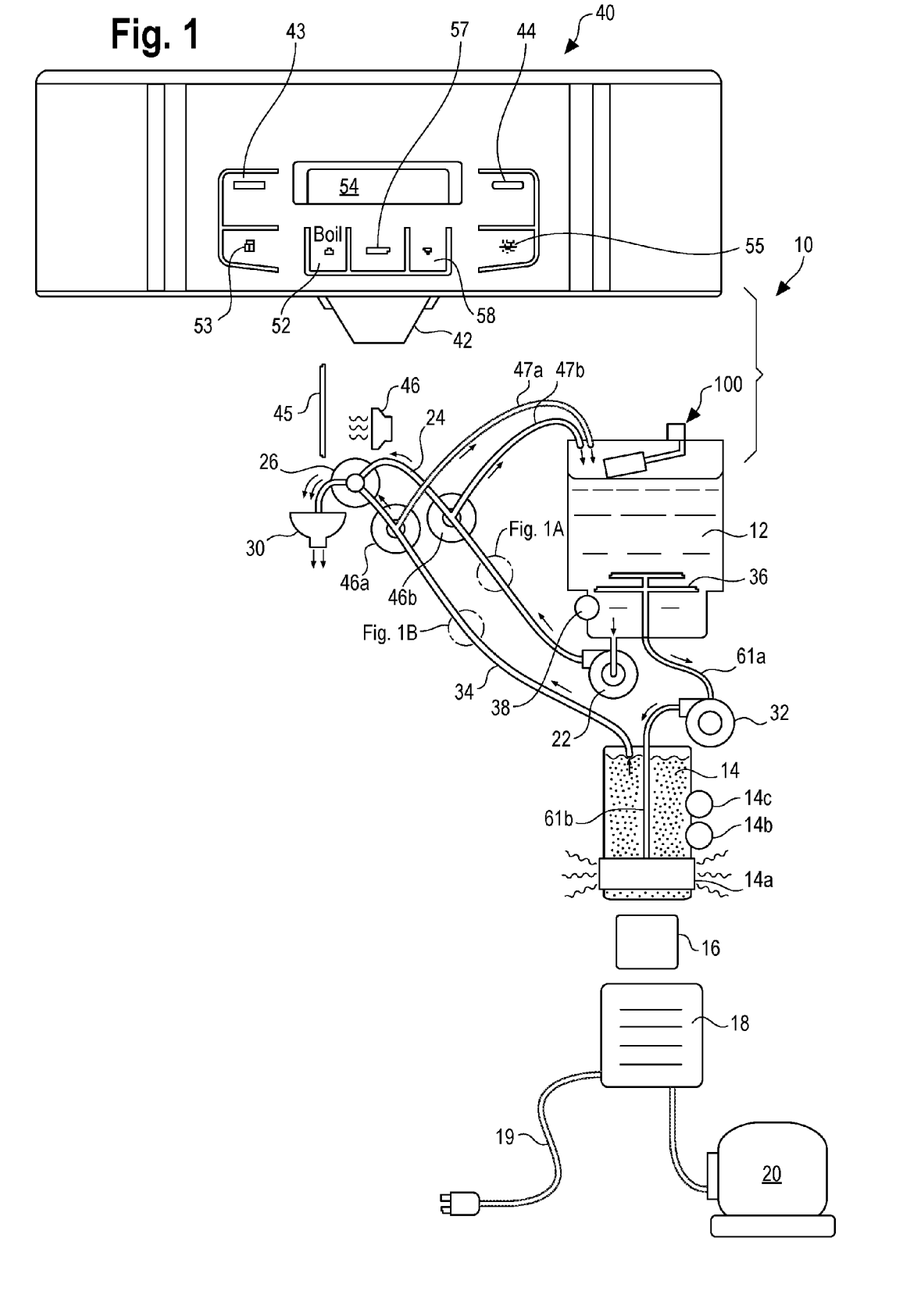
FIG. 1 is a schematic diagram of one preferred embodiment of the present invention.

Referring first to FIG. 1, one preferred embodiment of the water cooler system of the present invention, generally referred to by reference numeral 10, is shown. Water cooler system 10 may generally include cold tank 12, hot tank 14, float system 100 for detecting a water level in tank 12, transformer or power adapter/switching power supply 16, control PCB 18, and compressor 20. (A float system 100 may be used for a point-of-use (POU) system supplied by pressurized water instead of a bottled water. The float system may be replaced/exchanged with the alternate system disclosed here for the bottle water version application, with the rest of the system remaining the same. For example, if a "bottom load" system is used in which the water bottle is located below the dispenser, a pump may be used to move the water to the cold tank, and a float system may be used to regulate when to turn on/turn off the pump based on the sensed level in the cold tank.) In an alternative embodiment, a water regulating component commercially known as "EZ-Fill" may be used in connection with inverted bottle dispensing.

Still referring to FIG. 1, by energizing cold water pump 22 and cold-side, 3-way solenoid valve 46b (which may also be a mechanical valve), cold water may be pumped from the cold tank through cold water dispensing tubing 24, and then may be dispensed using 3-way solenoid 26, in a manner well known in the art, at spout 30. Alternatively, by energizing hot water pump 32 and hot-side, 3-way solenoid valve 46a (which may also be a mechanical valve), hot water may be pumped from the hot tank through hot water dispensing tubing 34, and then dispensed in a similar manner to that of the cold water.

Cold tank 12 may include a baffle 36, which may but need not be the type of baffle disclosed in copending U.S. Ser. No. 12/555,866. Cold tank 12 may also include cold control sensor 38 which may be used to turn on/off compressor 20 in order to maintain the cold tank water at the desired temperature. Hot tank 14 may include a heater band 14a (which may, alternatively, be an internal heating element), a heat limiter 14b (e.g., a thermostat to cut off power if the hot tank temperature exceeds a predetermined temperature, such as 95° C./203° F.), and a NTC thermistor 14c, such as a negative temperature coefficient thermistor. (A thermocouple may be used here instead, to provide a similar function.) NTC thermistor 14c may be used to sense the temperature of the hot tank, electronically communicating with control PCB 18 to control the hot tank temperature to be (e.g.) 60° C./140° F. for energy-saving mode, 86° C./187° F. for normal hot water cycle, and 92° C./198° F. for purpose of boiling water.

Referring now to a top portion of FIG. 1, water cooler 10 may include a graphical (e.g., LCD) interface 40 such as shown, which may include: a safety lock indicator 42; hot (43) and cold (44) water indicators which may remain always on; an interface PCB 45 which may be used to mount all the tactile switches, LEDs and LCD, allowing the user to interface with the unit; a buzzer 46 for providing audible tones (which may have a decibel adjustment feature); and a boiling water button 52.

Figure 1A:
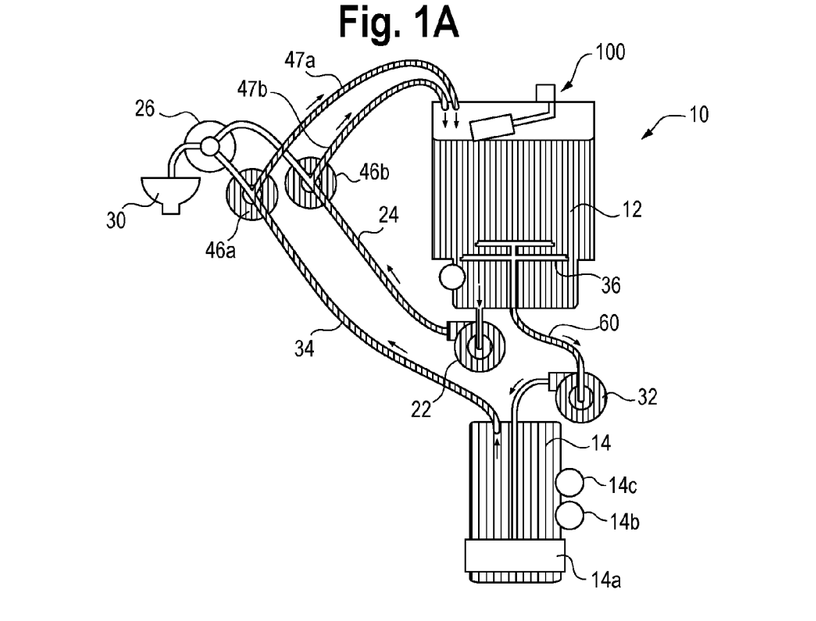
FIGS. 1A ("hot water Auto Clean" mode) and 1B ("hot water Manual Clean" mode) are schematic views of alternative modes that the embodiment shown in FIG. 1 may be placed in, illustrating exemplary locations which may be sanitized by hot liquid or heated gas, such as hot water or steam.
Figure 1B:
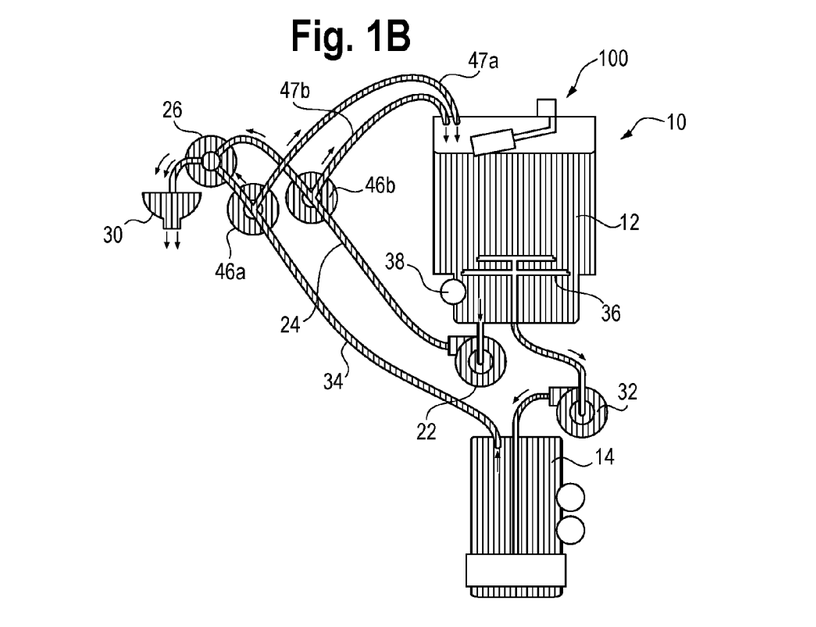

Referring now to FIGS. 1A and 1B, another feature of the present invention involves sanitizing the entire waterway system and wetted parts by heating up the system to a predetermined temperature (e.g., above 167-176° F. (75-80° C.)) using the already-existing heating element 14a used for hot tank 14 in system 10. Turning on hot water pump 32 only (not dispensing solenoid valve 26) may redirect the hot water back through tubing 47a to the cold tank, and raise the cold tank temperature. Circulating the heated water in the system for an appropriate time period may thus sanitize the entire waterway (including the hot waterway, the cold waterway, and pumps and solenoid valves) and the wetted parts that touch the heated water, as shown in FIG. 1B. This time period may vary, depending on the size of the cold tank. For example, a 3-gallon cold tank water took about 2.5-3 hrs to reach a temperature in the range of 167-176° F. (75-80° C.) using (e.g.) 450 W hot tank heater 14a, while a 1-gallon cold tank will take a shorter time. Using NTC 14c on the hot tank and cold control sensor 38 to control the heating time, when cold control sensor 38 reaches 167-176° F. (75-80° C.), the hot water sanitization cycle may be terminated). (If the hot water sanitization feature is applied to the embodiment shown in FIG. 2, both cold pump 22 and hot pump 32 should be energized at the same time to circulate the hot water back to the cold tank.)

Figure 2:
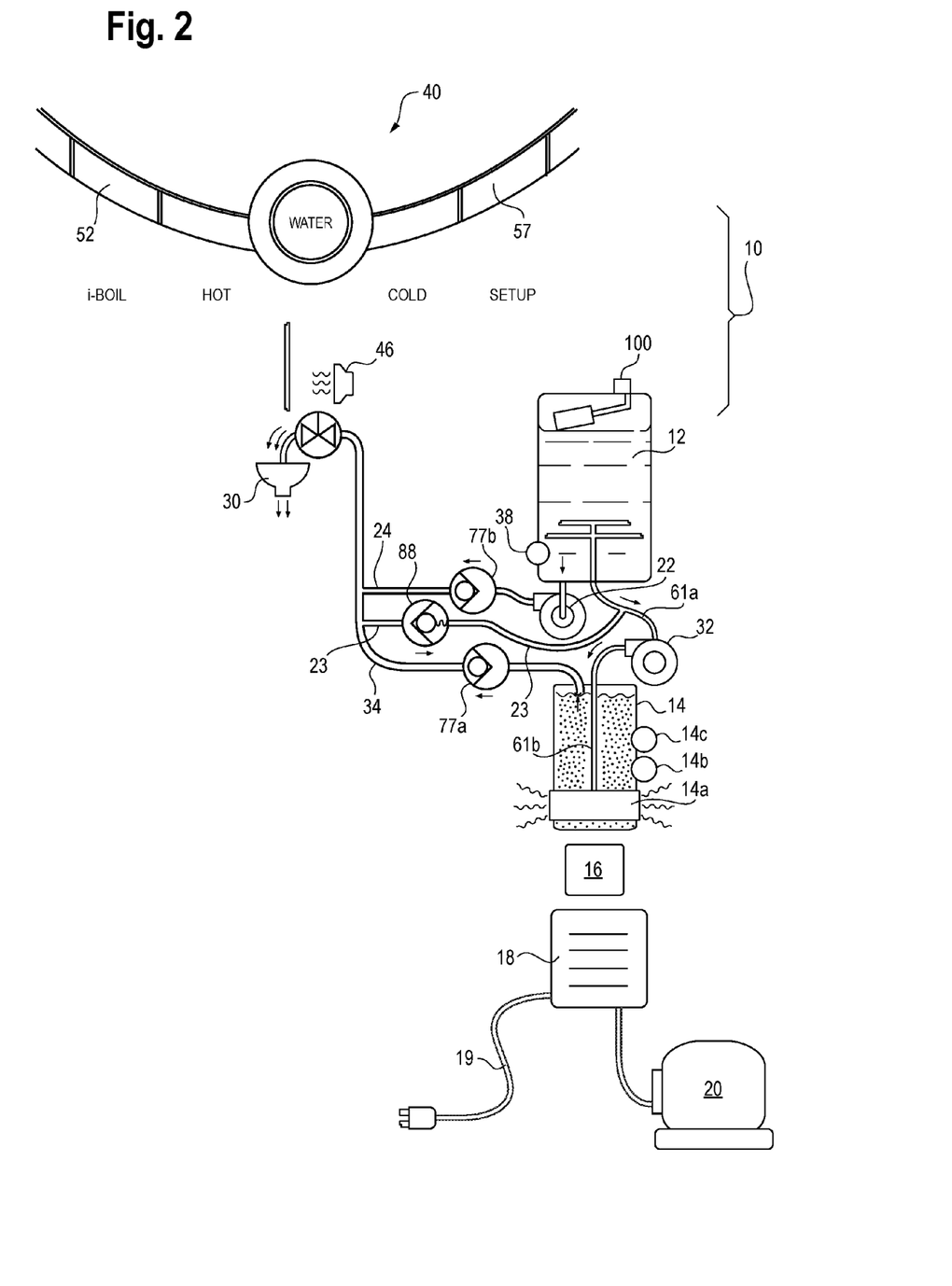
FIG. 2 is a schematic view showing another preferred embodiment of a liquid dispensing system of the present invention.

Referring now to FIG. 2, water cooler 10 may include a interface 40 such as shown, which may include: a water dispensing button 152; a LED ring indicator 153 for hot and cold which will only be lit when the Hot (red ring) or Cold (blue ring) water function is first selected, prior to depressing water dispensing button 152; an interface PCB 45 which may be used to mount all the tactile switches and LEDs, allowing the user to interface with the unit; a buzzer 46 for providing audible tones (which may have a decibel adjustment feature); and a boiling water button 52. Still referring to FIG. 2, the arrows on check valves 77a, 77b and 88 indicate flow direction. Cold pump 22 supplies liquid to cold tank 12 (which includes baffle 36 and float valve 100), while hot pump 32 supplies liquid to hot tank 14. Solenoid valve 26 coordinates dispensing of liquid through dispenser 30.

Using interface 40, for example, the sanitization processes described here are preferably accomplished automatically, either at predetermined periodic intervals as may be factory pre-set or as may be programmed by the user, or as the user may select.

Figure 3A:
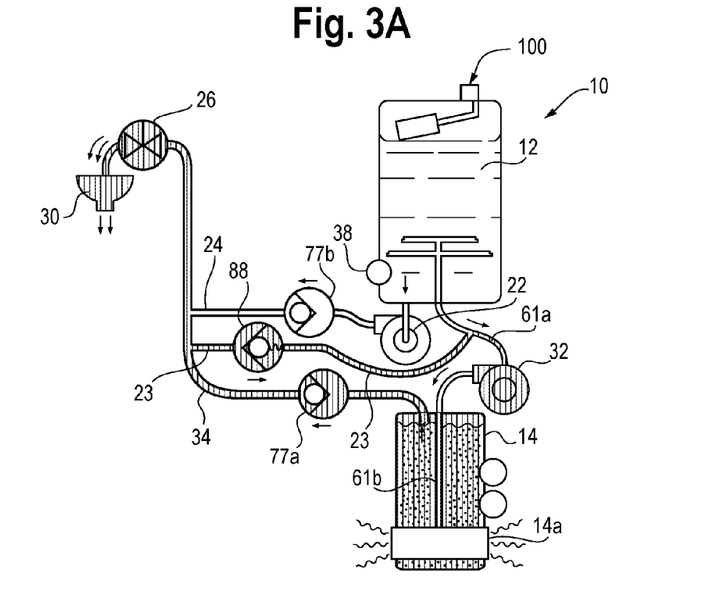
FIGS. 3A and 3B are schematic views of an alternative embodiment of a liquid dispensing system to that shown in FIGS. 1 and 1A, which may also be run in hot water "Auto Clean" and hot water "Manual Clean" modes, respectively.
Figure 3B:
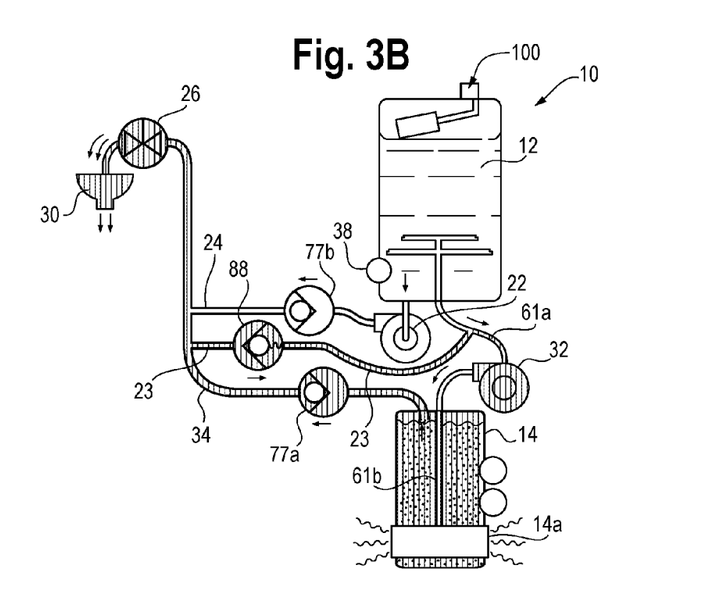

Referring now to FIGS. 3A and 3B, another embodiment is shown with an alternate waterway system to that of FIGS. 1A/1B, illustrating hot water or hot gas sanitizing of the entire, alternate waterway system and its wetted parts, such as by heating up the system to a predetermined temperature (e.g., above 167-176° F. (75-80° C.)) using the already-existing heating element 14a used for hot tank 14 in system 10. Like reference numerals between the FIGS. 1A/1B/2 and FIGS. 3A/3B embodiments indicate identical parts and functionality, unless otherwise indicated.

Referring now to the operation of the water dispensing system shown in FIG. 3B in the hot water Manual Clean sanitizing mode, with the hot water self-circulation sanitization feature activated, in an exemplary cycle the compressor may stop, and the hot tank may heat up to 86° C./187° F. and then cut out. The time and sanitization process may now begin. In an exemplary embodiment, starting from the 1-minute mark and continuing to the 30 minute mark, both the hot-side and the cold-side of the water pump may run 30 seconds every 1.5 minutes. The hot tank temperature may drop due to the replenished cold water going into the hot tank, and the heating cycle may start. After waiting for the next hot tank heating cycle to cut-off, an additional 40 minutes may then be added to the total heating time required for sanitization, referred to here as "S," in minutes (discussed further below). Heated water may then be circulated back to the cold tank through the hot and cold tubing/waterway during that time. After "S" total minutes, the system may then open the hot solenoid and the hot pump to dispense heated water from the hot side for 1 second, and may then open the cold solenoid and the cold pump to dispense heated water from the cold side for 1 second, and then repeat this cycle for 15 times. The heated water may flow through nozzle 30 and sanitize this area. The "Full Clean On" terminology may appear in display area 54 on the second line (see top of FIG. 1) when the Manual Full Clean mode self-circulation sanitization feature is activated.

Referring now to FIG. 3A, when the hot water Auto-Clean mode is selected, the hot water self-circulation sanitization feature may be activated, the compressor may stop, and the hot tank may heat up such as to about 86° C./187° F., and then cut out. The time and sanitization process may now begin. Starting from 1 minute and continuing to the 30-minute mark, both the hot-side and the cold-side of the water pump may run 30 seconds every 1.5 minutes. The hot tank temperature may drop due to the replenished cold water flowing into the hot tank, and the heating cycle may start.

After the next hot tank heating cycle cuts off, 40 minutes may be added to the total heating time "S" in minutes required for sanitization.

Figure 4:
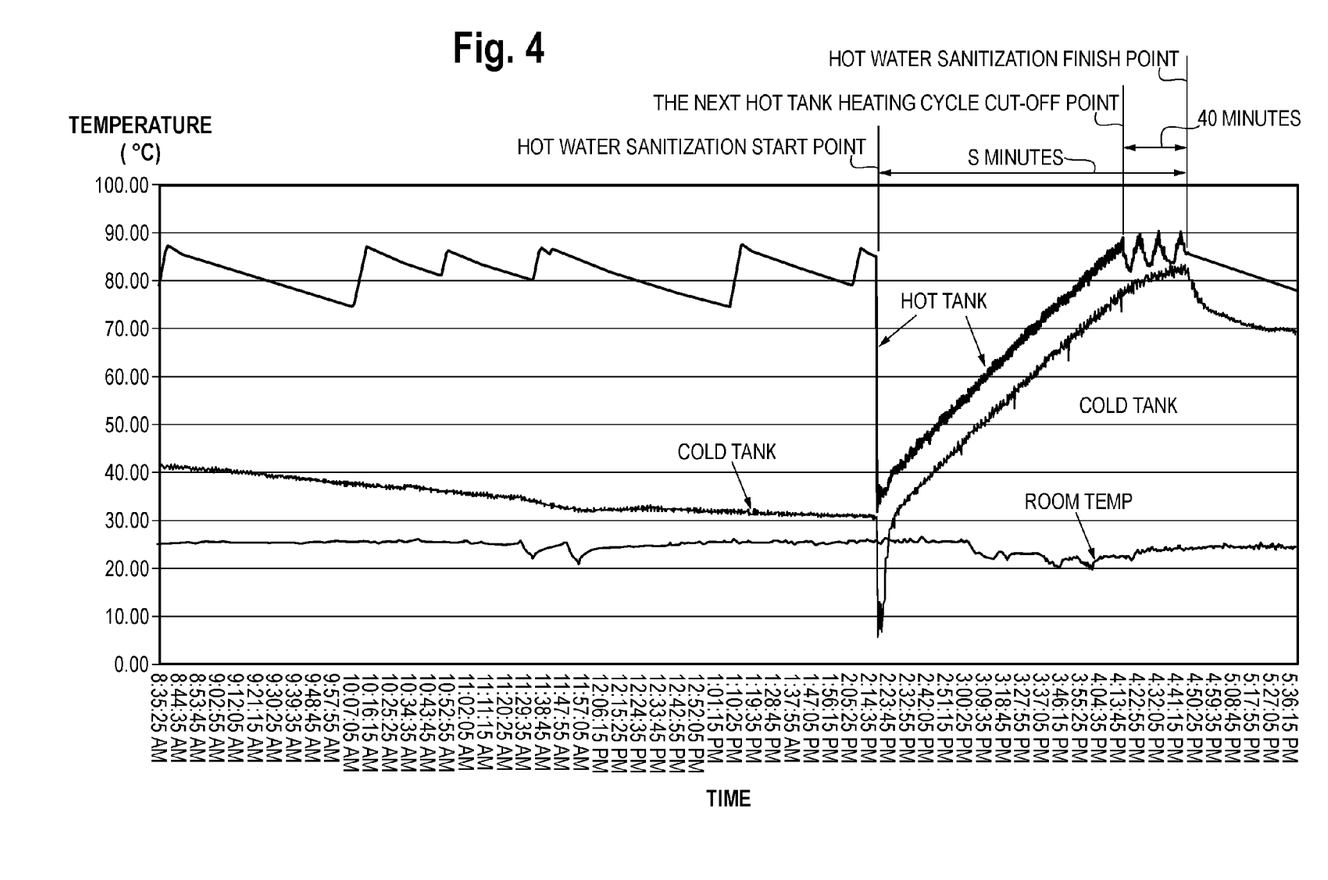
FIG. 4 is a graphical illustration of a preferred hot water sanitization heating cycle temperature profile.

Referring to a preferred hot water sanitization heating cycle temperature profile for a preferred embodiment, shown in FIG. 4, when actuating the hot water sanitization feature, the total time "S" required for sanitization varies depending on the water temperature in the system (cold tank and hot tank) at the time the sanitization feature is actuated: the lower the system temperature, the larger the "S" time value necessary to bring the system to the required temperature for sanitization.

Heated water may be circulated back to the cold tank through the hot and cold tubing/waterway during S minutes. In the Auto-Clean mode, no water flows out the nozzle to sanitize this area. The "Auto-Clean On" terminology may appear in the display on the second line.

In both Manual and Auto Clean modes, the system and hot tank temperatures are limited by the hot tank NTC. All waterways may be heated to at least 80° C. for 30 minutes to achieve sanitization. After "S" minutes, the system may get back to normal operational mode.

During the self-circulation sanitization process, both hot and cold dispensing buttons may be locked out, and all LEDs may be powered off, except the LCD display and backlight. "Auto Clean On" or "Full Clean On" terminology may be displayed in the LCD display. Attempts to dispense water by depressing the dispensing button may trigger a buzzer (e.g., 3 quick beeps in ½ second). Other setup features and buttons (e.g., Setup, Up, Down, Brightness) may still be used during this time.

To exit/stop the hot water self-circulation sanitization process (either Auto Clean or Manual Full Clean modes), the "Manual Full Clean" white button may be depressed and held for about (e.g.) 3 seconds until an audible tone is heard, at which point the system may return to normal operational mode.

Those of ordinary skill in the art will understand that a vessel, such as one capable of holding 4 cups (1 liter) of water, may be placed under the nozzle area during hot water sanitization to ensure that no liquid leaks during the sanitization process.

Current regulations, such as those from the FDA and the Arizona Department of Health Services, suggest that whether steam or hot water is used, the following times and intensities may be employed to provide sanitization: at least about 180° F. (82.2° C.) for at least about 20 minutes.

It should be understood that any hot water sanitizing liquid dispensing system according to the present invention may be used to sanitize the faucet/nozzle/dispensing mechanism, as desired. Additionally, externally-supplied steam may be used instead of, or in addition to, heated liquid to sanitize the waterways of the liquid dispensing system.

Referring to FIGS. 1B and 3B, in the "Manual Clean" and "Manual Full Clean" modes, a vessel that is (e.g.) capable of holding 4 cups (1 liter) of water may be provided. Referring to FIG. 1A, preferably the "Auto Clean" mode will run the self-circulation sanitization automatically based on the frequency and start time setup, with no user intervention required.

Referring to FIGS. 1A/1B and 3A/3B, in a preferred embodiment, when the Manual Full Clean mode or Auto Clean self-circulation sanitization feature is selected by the user, compressor 20 may stop, and both hot water pump 22 and cold water pump 32 may be run for 30 seconds every 1.5 minutes. The hot tank temperature will drop due to the replenished cold water flowing into the hot tank, and the heating cycle will start. After waiting for the next hot tank heating cycle to cut-off, and then waiting an additional 40 minutes, for a total heating time of "S" minutes, heated water may then be circulated back to the cold tank through the hot and cold tubing/waterway during these "S" minutes.

In a preferred embodiment, when the Manual Full Clean mode is selected by the user, after "S" minutes, the system will open the hot solenoid and the hot pump to dispense heated water from the hot side for 1 second, and then open the cold solenoid and the cold pump to dispense heated water from the cold side for 1 second, and repeat this cycle 15 times. The heated water will flow through the nozzle 30 and sanitize this area.

Referring to FIG. 1A, in another preferred embodiment, when the Auto Clean mode self-circulation sanitization feature is selected by the user, after "S" minutes, both the hot-side and cold-side 3-way solenoid valve 26 (2 in, 1 out) may not be permitted to open. With the FIG. 3A embodiment, when the Auto Clean mode self-circulation sanitization feature is selected by the user, after "S" minutes, both the hot-side and cold-side solenoid valve 26 (1 in, 1 out) may not be permitted to open.

In the preferred embodiment, during the self-circulation sanitization process, all dispensing buttons may be locked out, and all LEDs may be deactivated, except the LCD display showing the "Auto Clean ON" or "Full Clean ON" terminology. Attempts to dispense water may, for example, simply trigger a buzzer (e.g., 3 quick beeps in ½ seconds). Setup buttons may still be used in this mode, for example.

Referring to FIG. 1, in the exemplary embodiment, interface 40 may be provided with a button 53 with the "lock" icon, such that by pressing and holding this button, for example (and, e.g., waiting for an audible tone) can lock or unlock hot water dispensing, as desired. A brightness button 55 may also be provided, allowing the user to adjust the brightness of all LEDs and LCD displays (e.g., there may be three brightness modes: full, 50% and 10%).

Still referring to interface 40, depressing "setup" button 57 and (e.g.) waiting for an audible tone, can activate the setup mode. Now, by using "up" button 52 and "down" button 58, the desired settings (e.g., time, date, start, stop and frequency times for various functions such as sanitizing, auto clean, etc.) may be input. An "energy saved" switch (not shown) may also be provided, in order to lower the hot tank temperature (e.g., to 60° C./140° F.) during the night to save additional energy.

In an alternative embodiment, not shown in the drawings, the hot tank may be eliminated, such that the water cooler only provides room temperature and chilled water. In this embodiment, pump 32 may communicate directly with cold water tubing 34.

In an alternative embodiment, not shown in the drawings, liquid associated with a cooler may be sanitized by providing an add-on module to provide hot water, or manually pouring in or otherwise introducing hot water to the cooler waterways and allowing it to circulate, rather than drawing hot water from a dedicated hot water tank associated with the cooler.

The above description is not intended to limit the meaning of the words used in the following claims that define the invention. Other systems, methods, features, and advantages of the present invention will be, or will become, apparent to one having ordinary skill in the art upon examination of the foregoing drawings, written description and claims, and persons of ordinary skill in the art will understand that a variety of other designs still falling within the scope of the following claims may be envisioned and used. It is contemplated that these or other future modifications in structure, function or result will exist that are not substantial changes and that all such insubstantial changes in what is claimed are intended to be covered by the claims.

The following terms are used in the claims of the patent as filed and are intended to have their broadest meaning consistent with the requirements of law. Where alternative meanings are possible, the broadest meaning is intended. All words used in the claims are intended to be used in the normal, customary usage of grammar and the English language.

We claim:

1. A method for automatically sanitizing a liquid dispensing system having waterways providing paths for the liquid to flow to a dispenser, comprising the steps of:
providing cold and hot liquid storage tanks;
providing a first liquid pathway allowing chilled liquid to flow between the cold tank and the dispenser, and a second liquid pathway allowing heated liquid to flow between the hot tank and the dispenser;
providing one or more dispensing valves permitting hot and cold liquid to be selectively dispensed through the dispenser; and
sanitizing the waterways within the system, including the first and second liquid pathways, an interior surface of the cold and hot tanks, and an interior surface of the dispenser, when the one or more dispensing valves are closed, and no dispensing is occurring, by automatically introducing an ozone-containing, sanitizing liquid or gas to the waterways during a period when no dispensing occurs, wherein the step of introducing the ozone-containing, sanitizing liquid or gas occurs when a user manually places the liquid dispensing system into a sanitizing mode, thereby closing the one or more dispensing valves and contemporaneously locking out dispensing from occurring during the sanitization process.

2. The method of claim 1, wherein the step of introducing the ozone-containing, sanitizing liquid or gas is accomplished by providing a liquid or gas originating from a source outside of the system.

3. The method of claim 1, wherein the liquid dispensing system comprises either a pump-fed or a gravity-fed liquid dispensing system.

4. The method of claim 1, wherein the step of introducing the ozone-containing, sanitizing liquid or gas is accomplished by obtaining the liquid or gas from a source within the system.

5. The method of claim 1, wherein the step of introducing the ozone-containing, sanitizing liquid or gas occurs at predetermined periodic intervals.

6. A method for automatically sanitizing a liquid dispensing system having waterways providing paths for the liquid to flow to a dispenser, comprising the steps of:
providing cold and hot tanks, wherein liquid within the cold tank is cooled using a compressor, and wherein liquid within the hot tank is heated using intermittent heating cycles, with each cycle ending with a cut-off;
providing a first liquid pathway allowing chilled liquid from the cold tank to flow between the cold tank and the dispenser;
providing a second liquid pathway allowing heated liquid from the hot tank to flow between the hot tank and the dispenser;
providing a third liquid pathway allowing an unrestricted flow of heated liquid from the hot tank into the cold tank when a user has placed the liquid dispensing system into a sanitizing mode;
providing one or more dispensing valves permitting the hot and cold liquid to be selectively dispensed through the dispenser, and providing one or more liquid pumps permitting cold and hot liquid to be pumped from the cold and hot liquid storage tanks to the one or more dispensing valves; and
sanitizing the waterways within the system, including the dispenser, the cold and hot tanks, and the first, second and third liquid pathways, by providing heated liquid from the hot tank to the waterways, when the one or more dispensing valves are closed, and no dispensing is occurring, wherein the step of introducing the heated liquid occurs when a user manually places the liquid dispensing system into the sanitizing mode, thereby contemporaneously locking out dispensing from occurring during the sanitization process, and wherein during the sanitizing mode the one or more liquid pumps are energized causing cold liquid from the cold tank to flow into the hot tank and then, for a preselected time following the cut-off of the next heating cycle for the hot tank, causing the heated liquid to flow into and to sanitize the cold tank and the other waterways.

7. The method of claim 6, wherein the sanitizing liquid is heated to a temperature of between about 165° F. and 180° F., and using the liquid or gas to sanitize for at least about 20 minutes.

8. The method of claim 6, wherein the sanitizing liquid is heated to a temperature of at least about 180° F.

9. The method of claim 6, wherein the preselected time is about 40 minutes.

10. The method of claim 6, wherein the sanitizing step automatically occurs.

11. The method of claim 6, wherein the sanitizing step occurs when a user manually selects the step.

* * * * *